United States Patent
DeNuzzio et al.

(10) Patent No.: US 8,808,321 B2
(45) Date of Patent: Aug. 19, 2014

(54) INTEGRATED LANCET AND BODILY FLUID SENSOR

(75) Inventors: John D. DeNuzzio, Chapel Hill, NC (US); Steven Keith, Chapel Hill, NC (US); Lawrence A. Monahan, Willow Spring, NC (US); Phyllis Palmer, Durham, NC (US); Bill Stewart, Cary, NC (US); Todd M. Chelak, Waldwick, NJ (US); Robert E. West, Basking Ridge, NJ (US); William Allen, Houston, TX (US); Frederick Karl, Beaverton, OR (US); Lee Griswold, Norwalk, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 19 days.

(21) Appl. No.: 12/929,261

(22) Filed: Jan. 11, 2011

(65) Prior Publication Data

US 2012/0011705 A1   Jan. 19, 2012

Related U.S. Application Data

(62) Division of application No. 11/704,186, filed on Feb. 9, 2007, now Pat. No. 7,959,583, which is a division of application No. 10/259,798, filed on Sep. 30, 2002, now Pat. No. 7,192,405.

(51) Int. Cl.
   *A61B 17/14*   (2006.01)
   *A61B 17/32*   (2006.01)
   *A61B 5/00*    (2006.01)
   *B65D 81/00*   (2006.01)

(52) U.S. Cl.
   USPC .............................. 606/181; 600/583; 600/584

(58) Field of Classification Search
   USPC ............ 422/1, 22, 24, 50, 410, 430; 250/427, 250/432 R, 455.11, 492.1; 600/583, 584; 53/425, 450, 477; 606/181–183; 205/777.5; 204/403.01
   See application file for complete search history.

(56) References Cited

U.S. PATENT DOCUMENTS

| | | |
|---|---|---|
| 5,971,941 A | 10/1999 | Simons et al. |
| 6,071,251 A | 6/2000 | Cunningham et al. |
| 6,143,164 A | 11/2000 | Heller et al. |
| 6,506,168 B1 | 1/2003 | Fathallah et al. |
| 7,396,334 B2 * | 7/2008 | Kuhr et al. ............. 600/583 |
| 2002/0102739 A1 | 8/2002 | Nomura et al. |
| 2002/0130042 A1 | 9/2002 | Moerman et al. |
| 2003/0094384 A1 * | 5/2003 | Vreeke et al. ........... 205/777.5 |
| 2003/0191415 A1 | 10/2003 | Moerman et al. |

OTHER PUBLICATIONS

"Company News: Johnson's Cholesterol Kits Set", Andrea Adelson, New York Times, Jun. 30, 1994.

* cited by examiner

*Primary Examiner* — Brian Szmal
(74) *Attorney, Agent, or Firm* — Roylance, Abrams, Berdo & Goodman, L.L.P.

(57) ABSTRACT

A lancing device integrated with a sensing strip and method of making and using the same are provided. A lance and analyte sensing strip are combined in a single, preferably disposable, device. In a preferred embodiment, a slot is provided in a support member so the lance can be engaged by a lance driver and driven into the skin producing a bodily fluid sample from a wound. The sensing area of the sensing strip is adjacent to the wound location reducing dexterity requirements for patients.

6 Claims, 8 Drawing Sheets

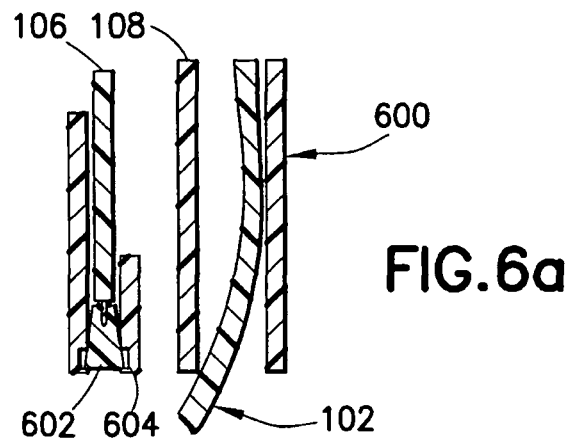
FIG.6a
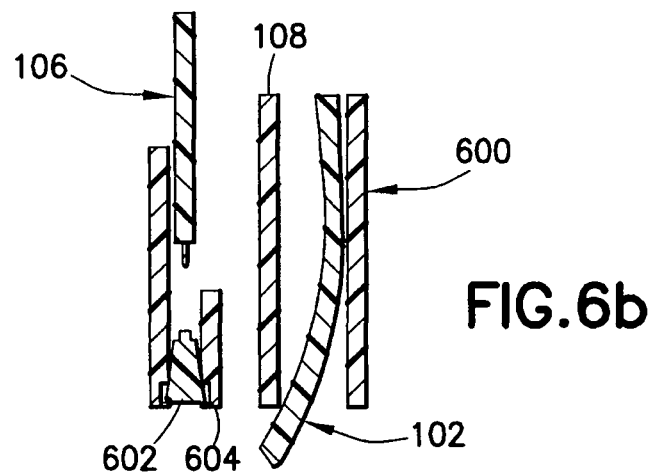
FIG.6b
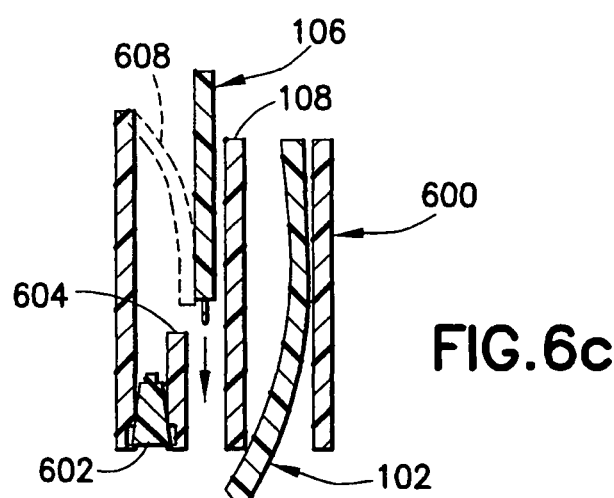
FIG.6c

INTEGRATED LANCET AND BODILY FLUID SENSOR

This application is a divisional of U.S. patent application Ser. No. 11/704,186, filed Feb. 9, 2007 now U.S. Pat. No. 7,959,583, which is a divisional of U.S. patent application Ser. No. 10/259,798, filed Sep. 30, 2002, which is now U.S. Pat. No. 7,192,405.

FIELD OF THE INVENTION

The present invention relates to bodily fluid collection and testing devices. In particular, the present invention relates to a device integrating a lancet and bodily fluid chemistry sensor to provide a single, preferably disposable unit.

BACKGROUND OF THE INVENTION

Conventional self-monitoring of blood glucose requires the patient to first load a lancet into a lancer and a separate test strip into a blood glucose meter. The lancer and lancet are then used to prick the finger, and a small drop of blood is squeezed to the surface. Finally, the sample port on the strip is brought into contact with the blood, and the sample is transported to the reaction zone on the strip via capillary action. This can be a labor-intensive, uncomfortable process that requires multiple devices and disposables. Further, patients must repeat this process several times a day in order to manage their disease properly.

Self monitoring of blood glucose is further complicated by the use of small-volume strips when the user is required to manipulate sub-microliter samples (<1 µl). It may be difficult for a person with diabetes to see and align a test strip with such a small sample, particularly for patients who are elderly or who otherwise do not have the dexterity of healthy individuals.

U.S. Pat. No. 5,971,941, to Simons et al., discloses a lancet and test strip integrated into a disposable cartridge. U.S. Pat. No. 6,143,164, to Heller et al., discloses a small volume in-vitro analyte sensor. U.S. Patent Application Publication No. US 2002/0130042 to Moerman et al. appears to discloses an apparatus for detection and quantization of an electrochemically detectable analyte, such as glucose, in blood or interstitial fluid, having a meter, a lancet and an electrochemical sensor. In one embodiment, an absorptive member is disposed to take up a sample of fluid from the pierced skin of the user without movement of the apparatus.

SUMMARY OF THE INVENTION

The present invention as exemplified in the embodiments disclosed herein, relates to a device that can be used to obtain a sample of bodily fluid for analyte measurement, having an integrated lancet and detection chemistry (sensor) in a single disposable unit. The unit is preferably sterilizable and compatible with cartridge dispensers. A device according to an embodiment of the invention first allows a droplet of bodily fluid to form on the skin, then ensures automatic alignment of the sample port to the bodily fluid droplet for transfer of the sample to the sample port and sensor surface. An embodiment of the invention uses wicking of the sample to improve sample transport and to remove bodily fluid from wound site.

Another embodiment of the invention is a device for obtaining a sample of bodily fluid by first piercing the skin so that the resulting bodily fluid directly enters a sensor, such as an electrochemical glucose sensor. The device integrates a lancing mechanism and a sensing mechanism, and is preferably adapted to be used with a glucose meter. Thus, a movable lancet or needle is constructed so that it mates with a glucose test strip. The combination device is positioned next to a user's skin so that the wound created by the lancet or needle is designed to be located a precise distance from the operating surface of the sensing strip. The drop of bodily fluid formed by the lancing action impinges on the sensing strip when it reaches a critical size. In one embodiment, the strip employs a capillary tube or a wick to carry the bodily fluid to the sensing surface. The distance from the skin surface to the sensing surface is preferably less than about 2 mm.

BRIEF DESCRIPTION OF THE DRAWINGS

The invention will be more readily understood with reference to the embodiments illustrated in the attached drawing figures, in which:

FIG. 2b is a cross-sectional side view of the cartridge of FIG. 2a;

FIGS. 6a-6c are cross sectional views of an embodiment of the present invention;

In the drawing figures, it will be understood that like numerals refer to like features and structures.

DETAILED DESCRIPTION OF THE INVENTION

Figure 1A:
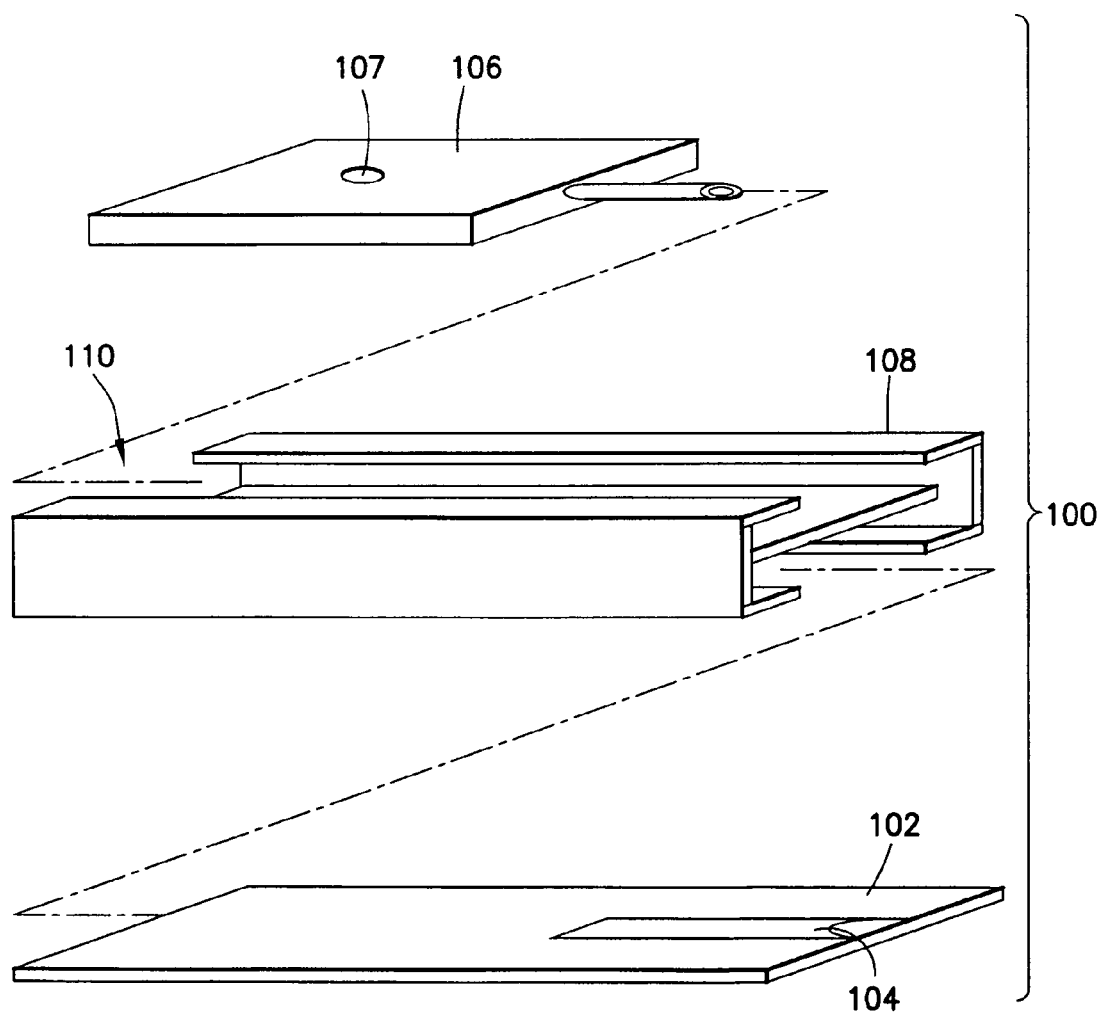
FIGS. 1a to 1d illustrate a first embodiment of the present invention employing a flat support member fitted with guides for a lancet and test strip.

The preferred embodiments of the invention will now be described with reference to the attached drawing figures. FIG. 1a illustrates a first embodiment of the present invention. The device 100 comprises a sensing strip 102, a rigid plastic strip similar to currently marketed glucose strips. Preferably, one face of the strip holds sensing components 104. In the embodiment illustrated in FIG. 1a, the sensing strip 102 is incorporated into a flat support member 108. The support member 108 has a slot 110 incorporated therein to allow access to a lancet 106 within. The lancet 106 is adapted to be engaged by a lancing device (not shown). The lancet 106 is preferably manufactured with a hole 107 to be engaged by the lancing device. Of course, the lancet 107 could also be manufactured with a detent, or any other similar structure adapted to be engaged by a lancing device and remain with in the scope of the invention. The hole is described herein as corresponding to the currently preferred embodiment of the invention. During use, the lancet 106 is driven into the skin and then retracted so that the resulting wound is free to release bodily fluid or bleed.

Strip 102 is preferably inserted into support member 108 during manufacturing. However, in an alternate embodiment of the invention, support member 108 is manufactured to accept a sensing strip 102, but the sensing strip remains separate until the device 100 is prepared for use. In this embodiment, the strip 102 is preferably kept sterile and inserted into the support member 108 before use. The strip 102 is preferably fixedly attached to support member 108 when installed.

Figure 1B:
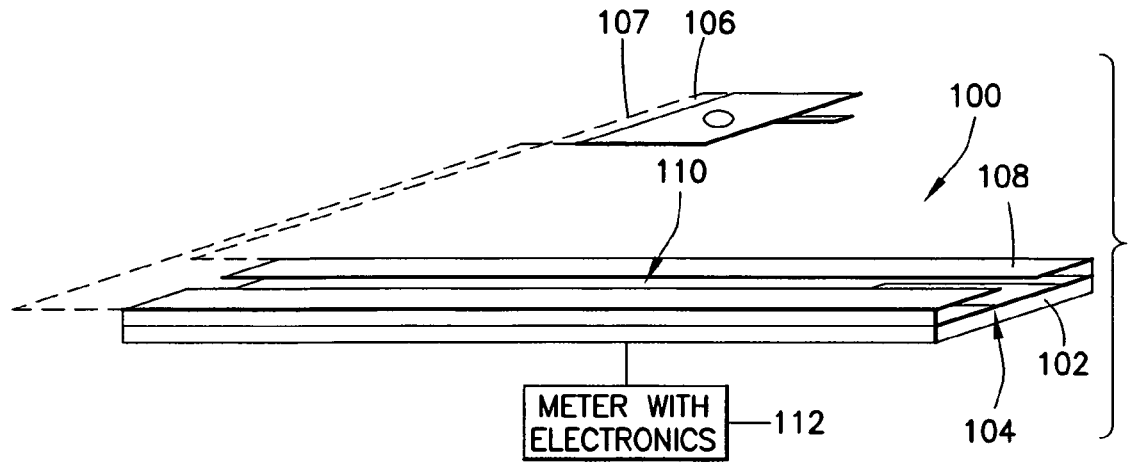

The sensing components 104 preferably employ electrochemical means for sensing an analyte, such as glucose, but other means of sensing analytes which are known in the art are to be considered within the scope of the present invention. In the case of an electrochemical sensor, the chemistry is arranged to make contact with conductive strips (not shown) such that in the presence of bodily fluid a circuit is completed. The term "bodily fluid" used herein will be understood to include blood, interstitial fluid, and combinations thereof. The conductive strips in turn provide electrical contact with the meter portion of the device 112 as shown in FIG. 1*b*. The electronics of the metering device 112 are preferably adapted to provide a voltage across the sensing area 104 and measure current through the circuit created in the presence of a bodily fluid sample.

Figure 1C:
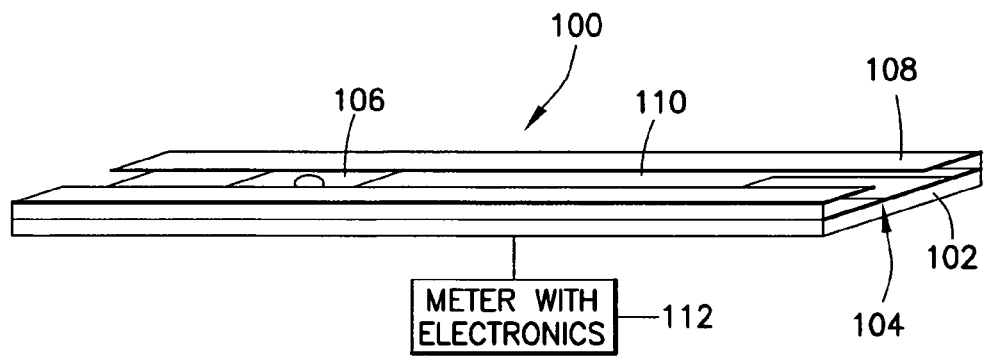
Figure 1D:
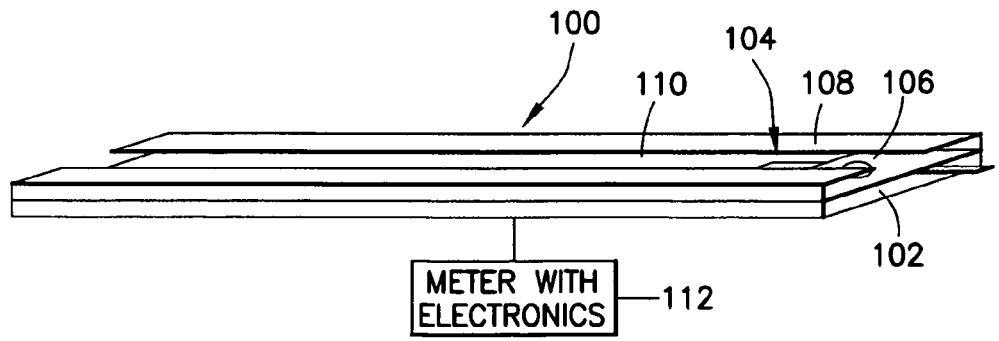

FIG. 1*c* illustrates the device 100 in a first configuration, with the lancet 106 stored within the cartridge 108, such that the lancet is not exposed outside the support member 108 to pose an accidental prick hazard. FIG. 1*d* illustrates the device 100 in a second configuration, with the lancet 106 exposed. A combination lancet driver and glucose meter (not shown) engages the lancet 106 through slot 110, and drives the lancet 106 from the first position to the exposed position to cause a wound, and then withdraw the lancet 106 from the wound to facilitate bleeding, and the subsequent formation of a bodily fluid droplet.

Glucose sensing strips typically employ a capillary flow to transport bodily fluid to the sensing chemistry. In the current device, a capillary flow is also preferably employed, and the strip 102 is initially positioned within the support member 108 such that the capillary flow tube contacts the droplet of bodily fluid generated by the lancet 106. The bodily fluid volume needed is preferably less than 0.5 µl. Adequate volume can be obtained from the fingertip or even off the fingertip, such as on the inner or outer forearm, using relatively pain-free lancets. Bodily fluid flow from a small lancet or needle can be enhanced by a properly designed supporting structure. Typically, an annular structure is brought to bear against the skin with an opening sized to spread the skin with a certain tension such that the wound will be held open after penetration. Bodily fluid is also pushed to the wound by the pressure of holding the device to the skin. In the preferred embodiment of the present invention, the opening and the sensing strip are appropriately positioned relative to each other such that the formation of the bodily fluid drop is optimally positioned for use by the sensing strip.

The strip 102 also preferably contains a wicking device, such as cellulose or nylon fibers, such that bodily fluid emerging from the skin immediately contacts the wick and is transported to the sensing surfaces 104. Such a wick also has the function of removing most bodily fluid from the skin surface, leaving a clean wound site requiring less subsequent activity by the user of the device.

A device according to the embodiment of FIGS. 1*a*-1*d* simplifies the monitoring process by combining a lancet 106 and a test strip 102 into a single disposable unit, and by combining the lancer and meter into a single device. During the monitoring process, the sample port of the strip becomes automatically aligned with the bodily fluid sample, so there is minimal patient intervention required. The integration of lancing and testing into a single unit greatly simplifies the glucose monitoring process.

The device illustrated in FIGS. 1*a*-1*d* improves upon the prior art by requiring fewer actions by the user. The device also advantageously utilizes small volumes of bodily fluid which allow off-finger testing. Furthermore, the device is advantageous in that it contains the bodily fluid sample in a disposable container, and requires only one part as opposed to two. The device also allows for sterilization of the lancet 106 during manufacture without adversely affecting the sensing portion 104 of the device. Examples of sterilization techniques which can adversely affect an electrochemical test strip include electron beam radiation and gamma radiation.

Using prior art devices, a user typically must first pierce his or her skin with a lancing device, then bring to bear a separate electrochemical sensor contained in a separate or the same housing. With the current device, the lancing and sampling activities are performed using one device and require fewer user actions. Advantageously, there is no requirement for the user to reposition the sensing chemistry over the bodily fluid droplet.

Existing glucose monitors utilize a volume of blood which has previously been brought to the skin surface after application of a separate lance. The lance and sensing strip are typically contained in separate housings, and may also be contained in one housing, but are always separate parts. In the device of FIGS. 1*a*-1*d*, the skin piercing and the sensing components are contained in one complete and disposable cartridge. The device 100 is preferably sized to contain most or all of the bodily fluid produced by the lancing action, leaving less residue on the skin or device for the user to deal with. The blood is thereby contained in a disposable and safely handled item.

The device of FIGS. 1*a*-1*d* allows independent fabrication of the sensing component and the lancing component up to a certain point in the manufacturing process where they are mated. This allows for sterilization of the lancing component without adversely affecting the sensing component (e.g. the enzymes used for electrochemical sensing of glucose). In certain embodiments of the device, the lancet may be encased in a plastic cap to maintain sterility. The cap is removed by the user or by the lancing device prior to use.

In a preferred embodiment of the invention, a plurality of the devices shown in FIGS. 1*a*-1*d* are packaged as part of a cartridge which is adapted to be inserted into a lancer or combination lancer and meter. The cartridge design is variable depending on the geometry of the lance and testing strip assembly. Stacked flat assemblies as shown in FIGS. 1*a*-1*d* are preferable. However, different arrangements, such as spokes on a wheel, or short tubes stacked within a longer tube, should be considered within the scope of the invention.

Figure 2A:
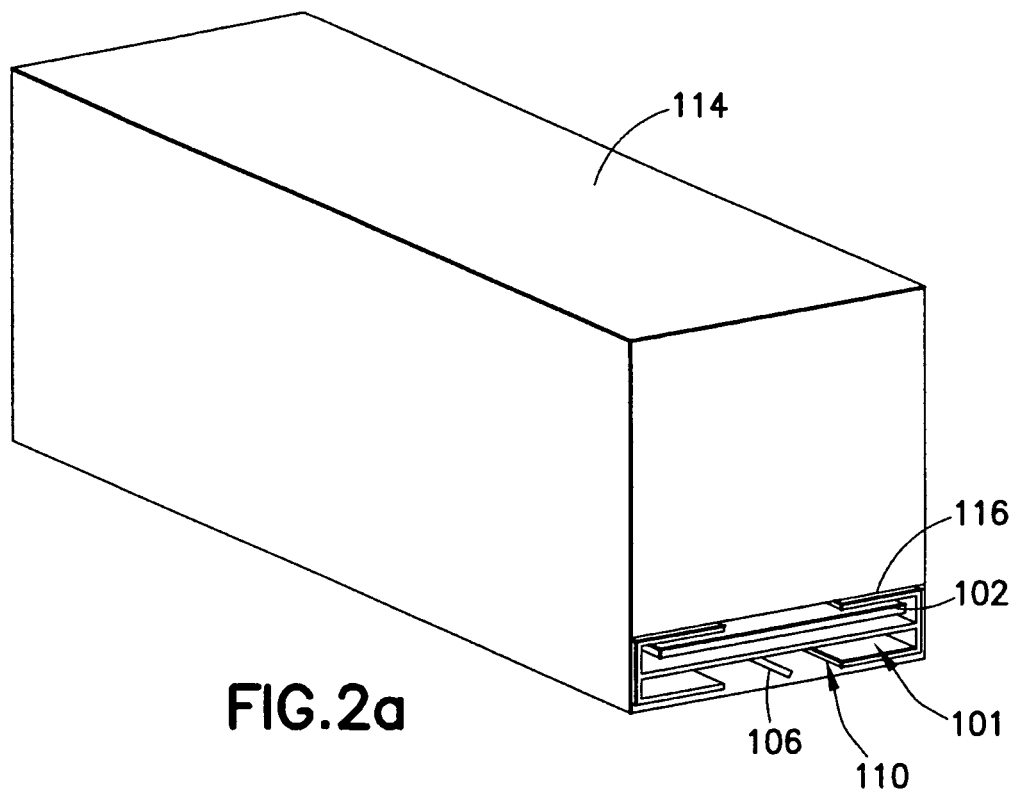
FIG. 2a is a perspective view of a cartridge containing lance and test strip assemblies according to an embodiment of the present invention.
Figure 2B:
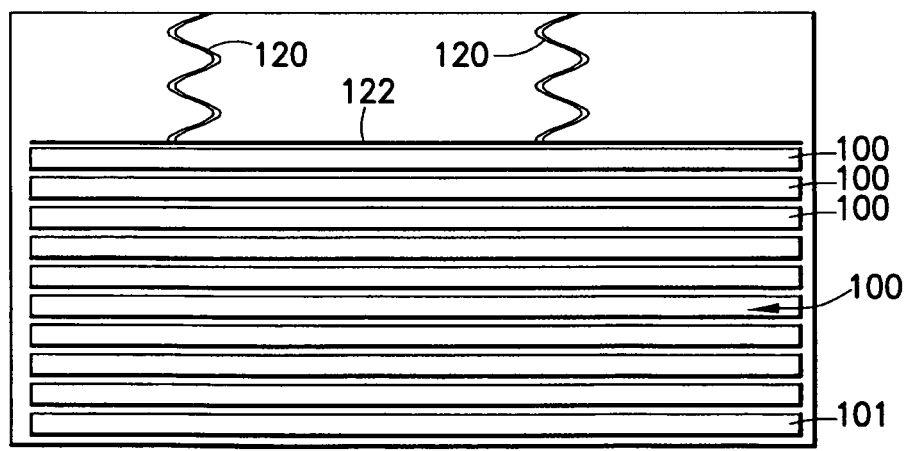
Figure 2C:
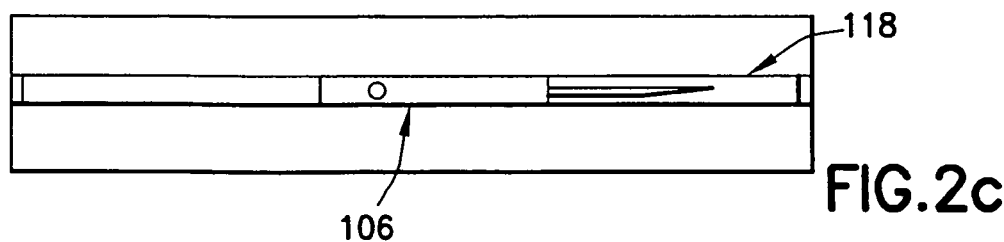
FIG. 2c is a bottom view of the cartridge of FIGS. 2a and 2b.

In the presently contemplated best mode of the invention, a plurality of the devices 100 illustrated in FIGS. 1*a*-1*d* are packaged in a cartridge 114 as illustrated in FIGS. 2*a*-2*c*, ready for insertion into a handheld, portable glucose meter. As shown in FIG. 2*a*, the cartridge 114 has an opening 116 adapted to allow access to the sensing surface 104 of the bottom-most assembly 101 in the stack. Opening 116 is also used to eject the bottom-most assembly 101 after use. Alternatively, opening 116 can be used to eject the bottom-most assembly 101 prior to use in a portable glucose meter.

The lance and test strip assemblies 100 are preferably oriented within cartridge 114 such that slot 110 is aligned with a slot 118 in the bottom of cartridge 114 as shown in FIG. 2c. Also, springs 120 and plate 122 keep the stack of assemblies 100 positioned at the bottom of the cartridge such that the bottom-most assembly 101 is aligned with opening 116 and slot 118. In this manner, the portable glucose meter (not shown) has access to, and can drive the lance 106 within the bottom-most assembly 101. Used devices are retained in a sealed portion of the meter for disposal, or are automatically ejected from the meter without requiring handling by the user. Existing technology for the electrochemical detection of glucose or other analytes can be utilized for the sensing strip portion of the device.

Figure 3:
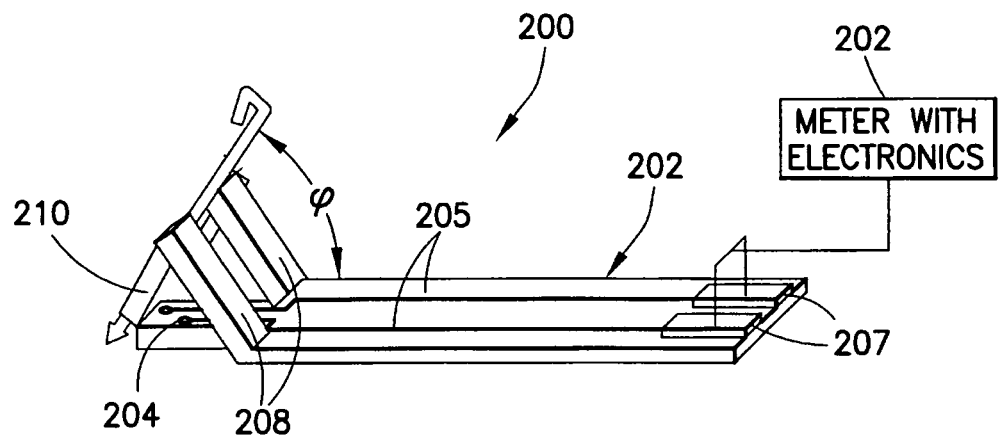
FIG. 3 illustrates a second embodiment of the present invention employing a flat support member with cantilever arms so that the direction of lancing can be offset from the plane of the strip.

FIG. 3 illustrates an alternate embodiment of the present invention that advantageously allows the angle φ between the direction of movement of the lancet and the plane of the sensing surfaces to be variable. The device 200 comprises a generally flat strip 202 having a sensing area 204. Electrical conductors 205 are connected between the sensing area 204 and electrodes 207 for connection to the metering device 212. Flat strip 204 serves structurally as a primary support member for cantilever members 208 and lancet support member 210. Lancet 206 is attached to lancet support member 210. Prior to use, the device 200 is preferably configured in a flat manner to allow several devices to be packaged in a cartridge 114 as inserts to a portable meter device. Bendable arms 208 and 210 are preferably manipulated once the strip is engaged in the lancer or meter. This design allows for optimization of the angle φ between the two parts of the device during use.

A stack of assemblies 200 can be advantageously packaged in a cartridge 114 while in their flat configuration. The bottom-most assembly is partially or fully ejected from the cartridge 114 through opening 116 in order to manipulate the device into the angled orientation shown in FIG. 3.

The lancet or needle can be sized according to the amount of bodily fluid desired. Preferably the bodily fluid volume needed is less than 0.5 μl. The penetrating portion of the lancet can be constructed from a flat or round blank. The transport of bodily fluid to the sensing surfaces is accomplished by any of a variety of means, including a capillary flow tube or a wick, or even a vacuum. The device can be used in conjunction with a handheld, portable lancer or meter, or can be made to function in as part of a larger test unit.

Figure 4A:
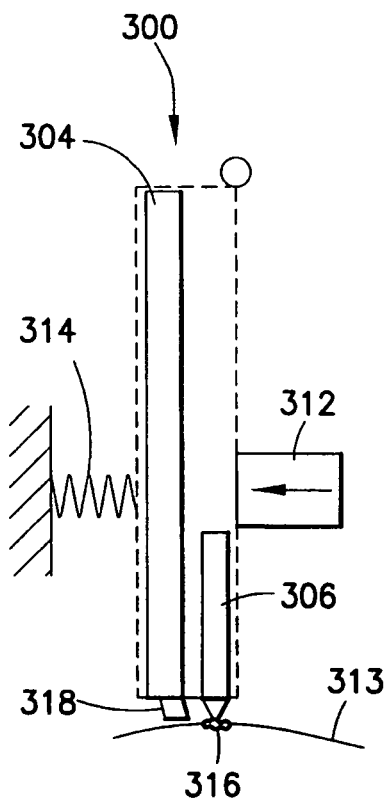
FIGS. 4a and 4b illustrate a third embodiment of the present invention wherein the test strip is brought into position for contact with the bodily fluid sample after the lancing action.
Figure 4B:
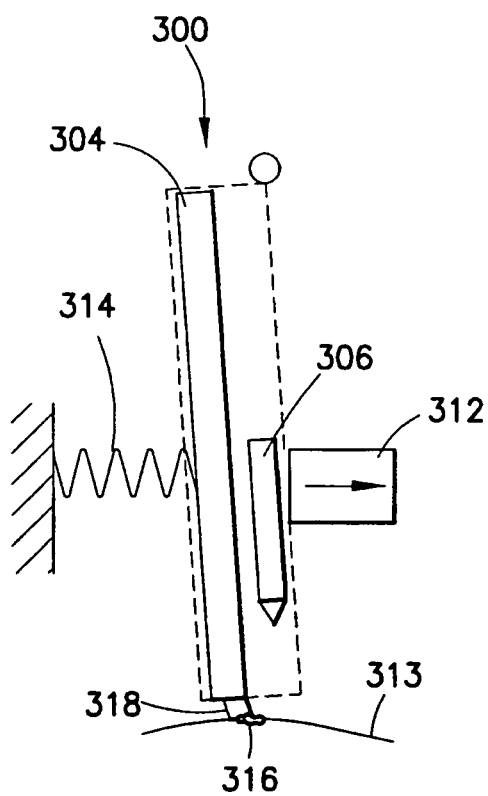

FIGS. 4a and 4b illustrate a device 300 according to a third embodiment of the present invention. In this embodiment, the device 300 automatically moves the sensing strip 304 into position after the lancet 306 is withdrawn from the skin. A lateral displacement of one to two millimeters is created by pressing a pushbutton 312 on the device support structure. The pushbutton 312 is used to trigger the lancet 306 when pressed, and also to displace the strip 304 when released.

FIG. 4a illustrates the device 300 after the pushbutton 312 has been pressed, releasing the lancet 306 into the skin 313. As pushbutton 312 is released, lancet 306 has been withdrawn from the skin, and spring 314 causes sensing strip 304 to be displaced to the location of the wound 316, as shown in FIG. 3b. A wick 318 is preferably included to aid bodily fluid flow to the sensing area by capillary action. Alternatively, an electromagnet or other automatic mechanism is be used to laterally or vertically displace the strip once a set period after lancing has elapsed.

Of course the embodiment shown in FIGS. 4a and 4b can easily be adapted for use in the cartridge 114 of FIGS. 2a-2c. In the cartridge configuration, spring 314 and pushbutton 312 preferably act on the cartridge 114, causing test strip 102 and in particular sensing components 104 on the bottom-most assembly within the cartridge to come into contact with a bodily fluid droplet that has formed on the surface of the skin after a predetermined about of time has elapsed to allow the droplet to form and achieve the desired volume.

The lancer or meter which uses any of the embodiments described herein can also embody design features that make sampling more reliable. An important aspect of bodily fluid sampling is to ensure proper pressure of the lancer housing on the skin. This ensures that the skin surface is positioned correctly relative to the axis of travel of the lancet and the orientation of the strip. This pressure also ensures reliable penetration depth of the lancet, which in turn ensures proper bodily fluid flow. Finally, this pressure also stretches the skin, keeping the wound open to ease bodily fluid flow. A pressure sensor on the lancer housing can be used to indicate to the user that the proper pressure has been achieved, and can also be part of an interlock system preventing premature lancing.

The lance and test strip can be positioned within the portable meter device in such a way that the distance between the piercing site and the sample port of the test strip are precisely spaced. Such a spacing allows adequate bodily fluid volume to build up on the skin before encountering the sample port.

Another advantage of the embodiments described above is that the lance and sensing strip portions of the device can be manufactured independently to a great degree. Thus, sterilization of the lancing tip can be achieved without concern for detrimental effects on glucose sensing chemistry, which can be manufactured with aseptic techniques. The two functioning components of the device are preferably "snap fit" together just prior to packaging to maintain the desired level of sterility.

Proper and precise alignment of the two parts may also be ensured by the lancer or meter. Thus, although each separate part may require precise fabrication, assembly of parts during manufacture does not require precise alignment. For example, in the design shown in FIG. 1a, the lance 106, test strip 102, and support member 108 can fit together loosely, and insertion of the device in the lancer or meter provides a precise structural support for each part.

It has been observed that it is much easier to get a bodily fluid sample to flow into a capillary tube if the drop is fully formed. If there is a break in the flow of bodily fluid in a capillary, the capillary action stops. It is also advantageous to create only one wave of bodily fluid flow over the sensing area. Electrochemical sensing relies on a constant delivery rate of glucose to the sensing components (e.g., enzymes). An interrupted flow of bodily fluid can create variable glucose delivery rates to the sensor, causing errors in measurement. Allowing sufficient bodily fluid to form within a drop on the skin before it is carried to the sensing surface (by, for example, a capillary or wick) reduces this source of errors. Moving the sensor strip onto the drop of bodily fluid as illustrated in FIGS. 4a and 4b ensures that variations in skin tension and height, which might cause variations in bodily fluid drop placement relative to the strip, do not cause premature entry of bodily fluid into the sensing area.

Figure 5:
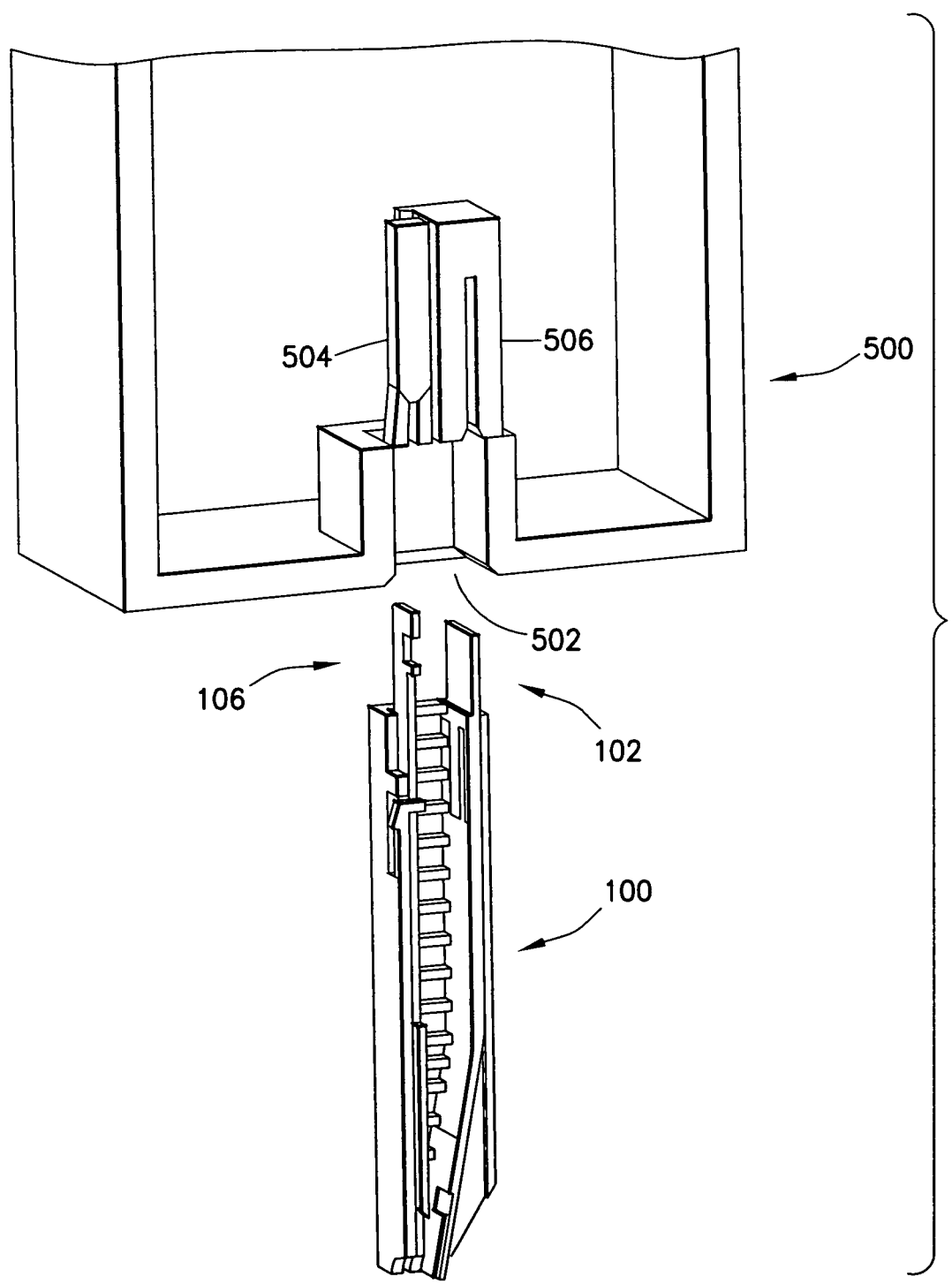
FIG. 5 illustrates a device according to the invention in use with a lancing device.

Another embodiment of a device 100 according to the present invention is shown in FIG. 5. The device 100 can be inserted into a combined bodily fluid meter and lancer 500. Combined meter and lancer 500 has an opening 502 adapted to accept the device 100. It also has a driver 504 that is adapted to receive and drive lance 106, and a strip receiver 506 that is adapted to receive the test strip 102. When the device 100 is inserted into opening 502, lance 106 becomes fixedly engaged in driver 504, and test strip 102 becomes fixedly engaged in strip receiver 506. In the illustrated embodiment, test strip 102 preferably has electrical contacts on the exposed proximal portion of test strip 102, which are arranged to make contact with corresponding electrical contacts in the strip receiver 506. Thus, when the device 100 is inserted into the combined meter and lancer 500, the strip 102 forms an electrical circuit with the meter.

Driver 504 is connected to driving means (not shown) that are adapted to cock the lance, drive it into the skin of a user, and withdraw the lance so that bodily fluid is free to flow from the small wound created by the lance.

FIGS. 6a-6c are cross sections of a device 600 according to another embodiment of the present invention. Lance 106 includes a cap 602 which protects the point of the lance prior to use. The cap 602 is preferably insert molded around the lance to maintain the sterility of the lance. The cap 602 is also preferably frangible so that it breaks away from the lance easily upon use. Device 600 includes a housing 108 that is adapted to contain the lance 106 and test strip 102. Housing 108 also includes a channel member 604 that creates separate channels for storing the lance and through which the lance travels when in use, as will be described in greater detail below. Housing 108 also preferably includes cap retaining slot 606 that holds the cap in a fixed location once the lance 106 and housing 108 are assembled. The proximal end of the lance 106 is allowed to protrude from the housing 108 to facilitate the lance 106 being engaged by the driver (not shown) in the combined meter and lancer 500.

When the device is cocked, lance 106 is first drawn in a proximal direction, causing frangible cap 602 to break away, exposing the lance point, as shown in FIG. 6b. As shown in FIG. 6c, housing 108 preferably contains a biasing means 608 such as a spring to force the lance into channel 610. Thus when lance 106 is driven into the skin of the user, it travels through channel 610.

Figure 7:
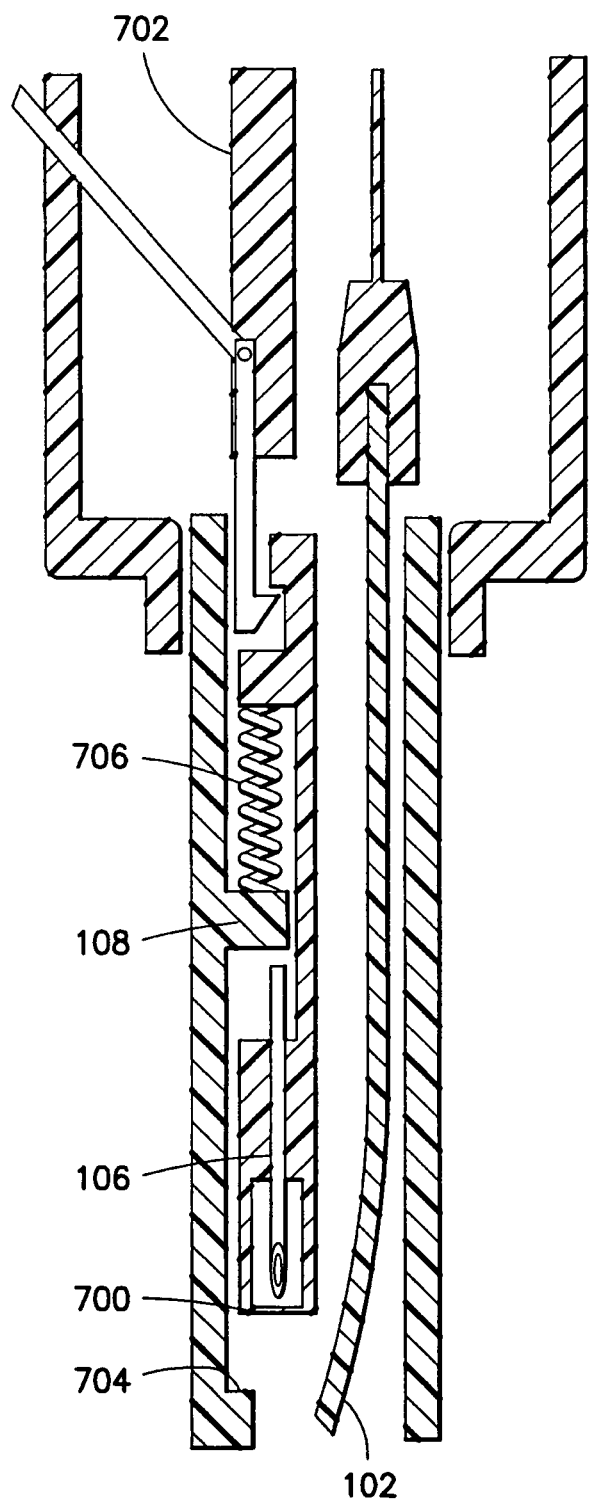
FIG. 7 is a cross sectional view of a lance and test strip assembly inserted into a lancing device according to another embodiment of the present invention.

It will be appreciated that many embodiments and variations are possible within the scope of the invention. FIG. 7 illustrates a cross-section of another embodiment of the invention. In this embodiment, the lance 106 is embedded in plastic 700 to remain sterile. The combined meter and lancer has a plunger 702 that attaches to the lance 106. When the plunger 702 drives the lance 106 into the skin of the user, plastic 700 is retained against ridge 704, so that lance 106 protrudes from plastic 700. In this manner, lance 106 remains sterile until it is actually used. A spring 706 is also preferably provided to help withdraw the lance 106 back into the device.

Figure 8A:
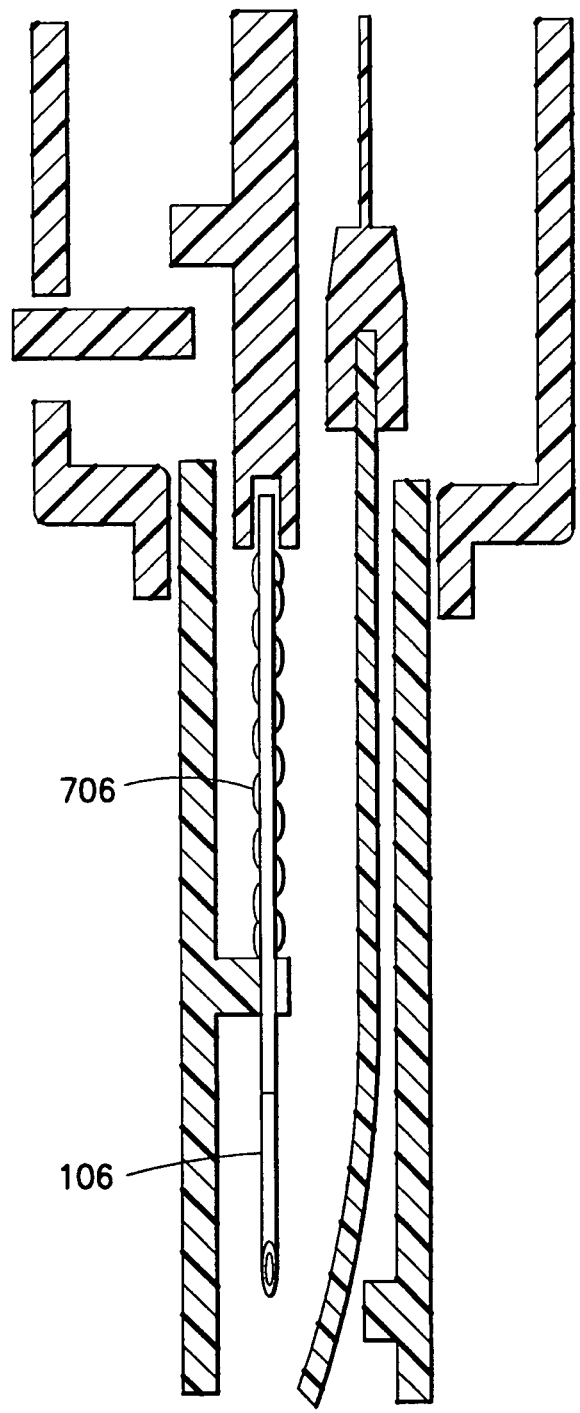
FIG. 8a is a cross sectional view of a lance and test strip assembly inserted into a lancing device according to another embodiment of the present invention.
Figure 8B:
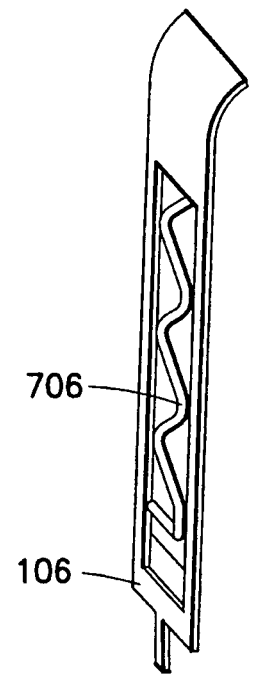
FIG. 8b illustrates a lancet with an integrally formed retention spring.

FIG. 8a illustrates an embodiment similar to FIG. 7, but wherein the retention spring 706 is incorporated into the lance 106. FIG. 8b illustrates a perspective view of the lance 106 of FIG. 8a having an incorporated retention spring 706.

While the invention herein disclosed has been described by means of specific embodiments and applications thereof, numerous modifications and variations can be made thereto by those skilled in the art without departing from the scope of the invention as set forth in the claims.

What is claimed is:

1. A method of manufacturing a bodily fluid sample acquisition and testing device, comprising the steps of:
   inserting a lance into a primary support member having an elongate slot arranged in an outside surface of said primary support member and extending from a proximal end of the primary support member to a distal end of the primary support member for accessing said lance through said primary support member from outside said primary support member,
   sterilizing said primary support member and lance; and
   after sterilizing said primary support member and lance, inserting a bodily fluid chemistry sensing strip comprising a sensing area into said primary support member such that said sensing area is adjacent to said lance.

2. The method of claim 1, wherein said sensing area is in electrical contact with two electrodes.

3. The method of claim 1, wherein said sterilization step comprises radiating said primary support member and lance with an electron beam.

4. The method of claim 1, wherein said sterilization step comprises radiating said primary support member and lance with gamma radiation.

5. The method of claim 1, wherein the slot is an open slot oriented in a driving direction of the lance.

6. The method of claim 1, wherein the step of inserting a bodily fluid chemistry sensing strip further comprises inserting the bodily fluid chemistry sensing strip into a secondary slot of the primary support member.

* * * * *